United States Patent [19]
Ozaki et al.

[11] Patent Number: 5,318,959
[45] Date of Patent: Jun. 7, 1994

[54] TRIAZOLE DERIVATIVES AS WELL AS INSECTICIDE AND ACARICIDE

[75] Inventors: Masami Ozaki; Atsuhiko Ikeda; Reijiro Honami; Takashi Yumita, all of Iwata; Naokazu Minoguchi, Ogasa; Hiroyuki Yano, Ogasa; Norihiko Izawa, Ogasa; Tadayoshi Hirano, Kakegawa, all of Japan

[73] Assignees: Kumiai Chemical Industry Co., Ltd.; Ihara Chemical Industry Co., Ltd., both of Tokyo, Japan

[21] Appl. No.: 956,984

[22] Filed: Oct. 6, 1992

[30] Foreign Application Priority Data

May 29, 1992 [JP] Japan ................... 4-161759

[51] Int. Cl.$^5$ ................ A01N 43/653; C07D 249/08; C07F 7/08
[52] U.S. Cl. .................... 514/63; 514/383; 548/110; 548/267.2; 548/267.4; 548/267.8; 548/268.6; 548/269.4
[58] Field of Search ................ 548/110, 267.2, 267.4, 548/267.8, 268.6, 269.4; 514/63, 383

[56] References Cited

U.S. PATENT DOCUMENTS

| | | | |
|---|---|---|---|
| 4,011,218 | 3/1977 | Baldwin et al. | 260/250 AH |
| 4,414,221 | 11/1983 | Parsons et al. | 514/383 |
| 4,788,210 | 11/1988 | Lüthy et al. | 514/383 |

FOREIGN PATENT DOCUMENTS 3631511 9/1986 Fed. Rep. of Germany.

OTHER PUBLICATIONS

Synthesis, (Jun. 1983), pp. 483-486, Perez et al, "Regioselective Synthesis of 1,2,4-Triazole and 1,2,4-Oxadizaole Deri . . . ".
Bulletin of the Chemical Society of Japan, vol. 56, pp. 545-548 (1983) Ito et al, "N-Methyl-N-(phenylsulfonyl)benzhydrazonoyl Chl . . . ".
Research Disclosure RD278004 (with abstract), "New 3,5-Di:Aryl-1-Methyl-1,2,4-Triazole Derivs. & Useful as Acaricides and . . . " (1967).

Primary Examiner—Patricia L. Morris
Attorney, Agent, or Firm—Stevens, Davis, Miller & Mosher

[57] ABSTRACT

A novel triazole derivative for use in an insecticide or an acaricide has a general formula [I]:

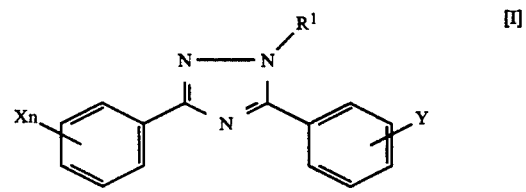

(wherein $R^1$ is an alkyl group, X is a hydrogen atom, a halogen atom, an alkyl group or the like, n is an integer of 1-5, Y is an alkenyl group, an alkynyl group, an alkoxyalkyl group or the like) and controls various injurious insects and mites, particularly mites and aphids without damaging crops.

21 Claims, No Drawings

TRIAZOLE DERIVATIVES AS WELL AS INSECTICIDE AND ACARICIDE

BACKGROUND OF THE INVENTION

1. Field of the Invention

This invention relates to novel triazole derivatives as well as insecticide and acaricide containing the same as an active ingredient.

2. Description of the Related Art

Japanese Patent laid open No. 56-154464 and DE-A-363-1511 disclose that various triazole derivatives develop insecticidal and acaricidal activities. However, it can not be said that the insecticidal and acaricidal activities of these compounds described in these specifications are satisfactory.

Up to the present, various compounds such as organophosphorus compound, organotin compound and the like have been used for the control of pests in farm and garden crops and mites. However, these compounds have been used for many years, so that the above injurious insects have a resistance to chemicals to a certain extent and it recently becomes difficult to control these insects. Particularly, this tendency is conspicuous in lepidopteran injurious insects, mites and aphids and becomes serious. As a result, it is demanded to develop new types of insecticide and acaricide having a different function.

SUMMARY OF THE INVENTION

The inventors have made various studies in order to create novel insecticides and acaricides having a very high effect against wide injurious pests and capable of safely using, which have never been found in the conventional technique, in the development of the insecticide and acaricide having a function different from that of the conventional ones.

Further, the inventors have synthesized various triazole derivatives and examined their physiological activities. As a result, the inventors have found that novel triazole derivatives having a general formula [I] as mentioned later have an excellent effect against wide injurious pests in farm and garden crops, particularly lepidopteran injurious insects, mites and aphids and also develop a very high effect against eggs and larvae of mites and larvae of aphids having a resistance to the conventional chemicals, and the invention has been accomplished.

According to the invention, there is the provision of a triazole derivative having the following general formula [I]:

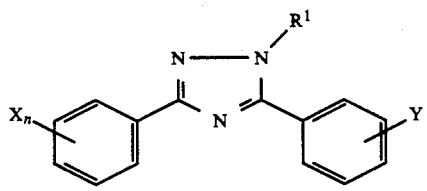

[wherein R¹ is an alkyl group, X is a hydrogen atom, a halogen atom, an alkyl group, an alkoxy group, an alkylthio group, a nitro group, a cyano group or a trifluoromethyl group, n is an integer of 1-5 provided that when n is 2 or more, X may be an optional combination of same or different atoms or groups, and Y is an alkenyl group, an alkynyl group, an alkoxyalkyl group, an alkoxyalkoxy group, an alkylthioalkyl group, a cycloalkyl group, a cycloalkylalkoxy group, a cycloalkylalkyl group, a cycloalkylalkenyl group, a cycloalkylalkynyl group, a trialkylsilylalkyl group, a trialkylsilylalkoxy group, an alkyl group having a carbon number of not less than 7, an alkoxy group having a carbon number of not less than 7, an alkylthio group having a carbon number of not less than 7, an alkylsulfinyl group having a carbon number of not less than 7, an alkylsulfonyl group having a carbon number of not less than 7 or a group represented by the following general formula (1):

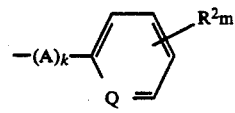

(wherein A is an oxygen atom, a sulfur atom, a lower alkylene group, a lower alkyleneoxy group, an oxy-lower alkylene group or a lower alkyleneoxyalkylene group, k is 0 or 1, Q is CH- group or a nitrogen atom, R² is a hydrogen atom, a halogen atom, an alkyl group, an alkoxy group, trifluoromethyl group or trifluoromethoxy group, m is an integer of 1-5 provided that when m is 2 or more, R² may be an optional combination of same or different atoms or groups)].

Furthermore, the invention provides an insecticide or an acaricide containing the above triazole derivative as an active ingredient.

Throughout the specification, the term "lower" means that the carbon number in the group added with this term is not more than 6.

Further, the term "alkyl group" means a straight or branched-chain alkyl group having a carbon number of 1-30, which includes, for example, methyl group, ethyl group, n-propyl group, isopropyl group, n-butyl group, isobutyl group, sec-butyl group, t-butyl group, n-pentyl group, isoamyl group, neopentyl group, n-hexyl group, isohexyl group, 3,3-dimethylbutyl group, n-heptyl group, 5-methylhexyl group, 4-methylhexyl group, 3-methylhexyl group, 4,4-dimethylpentyl group, n-octyl group, 6-methylheptyl group, n-nonyl group, 7-methyloctyl group, n-decyl group, 8 methylnonyl group, n-undecyl group, 9-methyldecyl group, n-dodecyl group, 10-methylundecyl group, n-tridecyl group, 11-methyldodecyl group, n-tetradecyl group, 12-methyltridecyl group, n-pentadecyl group, 13-methyl-tetradecyl group, n-hexadecyl group, n-heptadecyl group, n-octadecyl group, n-nonadecyl group, n-eicosyl group and the like.

The terms "alkoxy group", "alkylthio group", "alkylsulfinyl group" and "alkylsulfonyl group" are (alkyl-)—O— group, (alkyl)—S— group, (alkyl)—SO— group, and (alkyl)—SO₂ group in which the alkyl portion has the same meaning as mentioned above, respectively.

The term "halogen atom" means fluorine, chlorine, bromine and iodine.

The term "alkenyl group" means a straight or branched-chain alkenyl group having a carbon number of 2-20, which includes, for example, vinyl group, propenyl group, isopropenyl group, butenyl group, pentenyl group, hexenyl group, heptenyl group, octenyl group, 3-methyl-1-butenyl group, 4-methyl-1-pentenyl group and the like.

The term "alkynyl group" means a straight or branched-chain alkynyl group having a carbon number of 2-20, which includes, for example, ethynyl group, propynyl group, butynyl group, pentynyl group, hexynyl group, 3,3-dimethyl-1-butynyl group, 4-methyl-1-pentynyl group, 3-methyl-1-pentynyl group, 5-methyl-1-hexynyl group, 4-methyl-1-hexynyl group, 3-methyl-1-hexynyl group, heptynyl group, octynyl group, nonynyl group, decynyl group, undecynyl group, dodecynyl group, tridecynyl group, tetradecynyl group, pentadecynyl group, hexadecynyl group and the like.

The term "cycloalkyl group" means a cycloalkyl group having a carbon number of 3-12, which includes, for example, cyclopropyl group, cyclobutyl group, cyclopentyl group, cyclohexyl group, cycloheptyl group, cyclooctyl group and the like.

The term "cycloalkylalkyl group" means a cycloalkylalkyl group having a carbon number of 6-12, which includes, for example, cyclopentylmethyl group, cyclohexylmethyl group, cyclopentylethyl group, cyclohexylethyl group, cyclopentylpropyl group, cyclohexylpropyl group, cyclohexylpentyl group and the like.

The term "cycloalkylalkoxy group" means a (cycloalkylalkyl)—O— group in which the cycloalkylalkyl portion has the same meaning as mentioned above.

The term "cycloalkylalkenyl group" means a cycloalkylalkenyl group having a carbon number of 5-12, which includes, for example, cyclopentylvinyl group, cyclohexylvinyl group, 3-cyclopentyl-1-propenyl group, 3-cyclohexyl-1-propenyl group, 5-cyclohexyl-1-pentenyl group and the like.

The term "cycloalkylalkynyl group" means a cycloalkylalkynyl group having a carbon number of 5-12, which includes, for example, cyclopentylethynyl group, cyclohexylethynyl group, 3-cyclopentyl-1-propynyl group, 3-cyclohexyl-1-propynyl group and the like.

The term "tri(lower alkyl)silyl lower alkyl group" includes, for example, trimethylsilylmethyl group, dimethylethylsilylmethyl group, butyldimethylsilylmethyl group and the like.

The term "tri(lower alkyl)silyl lower alkoxy group" means [tri(lower alkyl)silyl lower alkyl]—O—group in which the tri(lower alkyl)silyl lower alkyl portion has the same meaning as mentioned above.

The term "lower alkylene group" means a straight or branched-chain alkylene group having a carbon number of 1-4, which includes, for example, —CH$_2$—, —CH$_2$CH$_2$—, —CH(CH$_3$)—, —CH$_2$CH$_2$CH$_2$—, —CH(CH$_3$)CH$_2$—, —C(CH$_3$)$_2$—, —CH$_2$CH$_2$CH$_2$CH$_2$—, —CH(CH$_3$)CH$_2$CH$_2$—, —CH$_2$CH(CH$_3$)CH$_2$— and the like.

The term "lower alkyleneoxy group" means -(lower alkylene)—O— group in which the lower alkylene portion has the same meaning as mentioned above.

The term "oxy-lower alkylene group" means —O—(lower alkylene)— group in which the lower alkylene portion has the same meaning as mentioned above.

The term "lower alkyleneoxyalkylene group" means —(lower alkylene)—O—(lower alkylene)— group in which the lower alkylene portion has the same meaning as mentioned above.

DESCRIPTION OF THE PREFERRED EMBODIMENTS

As a preferable compound according to the invention, there are mentioned compounds having the general formula [I] wherein $R^1$ is a straight or branched-chain alkyl group having a carbon number of 1-6, preferably methyl group, X is a hydrogen atom, a halogen atom, a straight or branched-chain alkyl group having a carbon number of 1-4, a nitro group, a cyano group or trifluoromethyl group, n is an integer of 1-3 provided that when n is 2 or 3, X may be an optional combination of same or different atoms or groups, Y is a straight or branched-chain alkyl group having a carbon number of 7-20, a cycloalkyl group having a carbon number of 3-12, a cycloalkylalkyl group having a carbon number of 6-12, a straight or branched-chain alkoxy group having a carbon number of 7-16, a cycloalkylalkoxy group having a carbon number of 7-12, a straight or branched-chain alkylthio group having a carbon number of 7-16, an alkylsulfinyl group, an alkylsulfonyl group, a straight or branched-chain alkenyl group having a carbon number of 3-16, a cycloalkylalkenyl group having a carbon number of 5-12, a straight or branched-chain alkynyl group having a carbon number of 3-16, a cycloalkylalkynyl group having a carbon number of 5-12, a tri(lower alkyl)silyl lower alkyl group, a tri(lower alkyl)silyl lower alkoxy group or a group represented by the formula (1) (wherein A is an oxygen atom, a sulfur atom, a lower alkylene group having a carbon number of 1-4, methyleneoxy group or oxymethylene group, k is 0 or 1, Q is CH- group or a nitrogen atom, $R^2$ is a hydrogen atom, a halogen atom, a lower alkyl group, a lower alkoxy group, trifluoromethyl group or trifluoromethoxy group, and m is an integer of 1-3 provided that when m is 2 or 3, $R^2$ may be an optional combination of same or different atoms or groups).

Concrete examples of the compounds having the general formula [I] according to the invention are shown in Tables 1 to 10. Moreover, the compound No. is referred in subsequent description.

TABLE 1

$$\text{Xn} \diagup\!\!\!\!\diagdown \text{—C(=N—N(R}^1\text{)—N=)—} \diagup\!\!\!\!\diagdown \text{Y}$$

| Compound No. | $R^1$ | Xn | Y | Melting point (°C.) or refractive index ($n_D^{20}$) |
|---|---|---|---|---|
| 1 | CH$_3$ | H | 4-C$_7$H$_{15}$ | 1.5819 |
| 2 | CH$_3$ | 2-F | 4-C$_7$H$_{15}$ | 1.5650 |
| 3 | CH$_3$ | 2-Cl | 4-C$_7$H$_{15}$ | 1.5816 |
| 4 | CH$_3$ | 2-Br | 4-C$_7$H$_{15}$ | 1.5924 |
| 5 | CH$_3$ | 2-I | 4-C$_7$H$_{15}$ | 1.6025 |
| 6 | CH$_3$ | 2,3,4,5,6-F$_5$ | 4-C$_7$H$_{15}$ | 1.5252 |
| 7 | CH$_3$ | 2-CH$_3$ | 4-C$_7$H$_{15}$ | 1.5803 |
| 8 | CH$_3$ | 2-OCH$_3$ | 4-C$_7$H$_{15}$ | 1.5840 |
| 9 | CH$_3$ | 2-SCH$_3$ | 4-C$_7$H$_{15}$ | 1.6003 |
| 10 | CH$_3$ | 2-CN | 4-C$_7$H$_{15}$ | 50.0-53.5 |
| 11 | CH$_3$ | 2-NO$_2$ | 4-C$_7$H$_{15}$ | 1.5780 |
| 12 | CH$_3$ | 2-CF$_3$ | 4-C$_7$H$_{15}$ | 1.5407 |
| 13 | CH$_3$ | 2-Cl | 4-C$_8$H$_{17}$ | 1.5800 |
| 14 | CH$_3$ | 2,6-F$_2$ | 4-C$_8$H$_{17}$ | 1.5532 |
| 15 | CH$_3$ | 2-Cl, 6-F | 4-C$_8$H$_{17}$ | 1.5652 |
| 16 | CH$_3$ | 2-Cl | 4-C$_9$H$_{19}$ | 1.5766 |
| 17 | CH$_3$ | 2-Cl, 6-F | 4-C$_9$H$_{19}$ | 1.5612 |
| 18 | CH$_3$ | 2,6-F$_2$ | 4-C$_9$H$_{19}$ | 1.5518 |
| 19 | CH$_3$ | 2,6-Cl$_2$ | 4-C$_9$H$_{19}$ | 1.5698 |
| 20 | CH$_3$ | 2-F | 4-C$_{10}$H$_{21}$ | 1.5595 |
| 21 | CH$_3$ | 2-Cl | 4-C$_{10}$H$_{21}$ | 1.5708 |
| 22 | CH$_3$ | 2-Br | 4-C$_{10}$H$_{21}$ | 1.5780 |
| 23 | CH$_3$ | 2-I | 4-C$_{10}$H$_{21}$ | 1.5875 |
| 24 | CH$_3$ | 2-CH$_3$ | 4-C$_{10}$H$_{21}$ | 48.0-50.0 |

TABLE 2

| Compound No. | $R^1$ | Xn | Y | Melting point (°C.) or refractive index ($n_D^{20}$) |
|---|---|---|---|---|
| 25 | $CH_3$ | 2-$OCH_3$ | 4-$C_{10}H_{21}$ | 1.5649 |
| 26 | $CH_3$ | 2-$SCH_3$ | 4-$C_{10}H_{21}$ | |
| 27 | $CH_3$ | 2-CN | 4-$C_{10}H_{21}$ | 37.0–40.0 |
| 28 | $CH_3$ | 2-$NO_2$ | 4-$C_{10}H_{21}$ | 55.0–58.0 |
| 29 | $CH_3$ | 2-$CF_3$ | 4-$C_{10}H_{21}$ | 56.0–57.0 |
| 30 | $CH_3$ | 2-Cl, 6-F | 4-$C_{10}H_{21}$ | 1.5570 |
| 31 | $CH_3$ | 2,6-$F_2$ | 4-$C_{10}H_{21}$ | 1.5482 |
| 32 | $CH_3$ | 2,6-$Cl_2$ | 4-$C_{10}H_{21}$ | 1.5678 |
| 33 | $CH_3$ | 2,4,6-$F_3$ | 4-$C_{10}H_{21}$ | 1.5340 |
| 34 | $CH_3$ | 2-Cl | 4-$C_{11}H_{23}$ | 52.0–54.0 |
| 35 | $CH_3$ | 2-Cl, 6-F | 4-$C_{11}H_{23}$ | 1.5495 |
| 36 | $CH_3$ | 2,6-$Cl_2$ | 4-$C_{11}H_{23}$ | 58.0–60.0 |
| 37 | $CH_3$ | 2,6-$F_2$ | 4-$C_{11}H_{23}$ | 1.5437 |
| 38 | $CH_3$ | 2-Cl | 4-$C_{12}H_{25}$ | 62.0–63.0 |
| 39 | $CH_3$ | 2-Cl, 6-F | 4-$C_{12}H_{25}$ | 51.0–52.0 |
| 40 | $CH_3$ | 2,6-$F_2$ | 4-$C_{12}H_{25}$ | 43.0–49.5 |
| 41 | $CH_3$ | 2,6-$Cl_2$ | 4-$C_{12}H_{25}$ | 53.0–54.5 |
| 42 | $CH_3$ | 2-Cl | 4-$C_{13}H_{27}$ | 55.0–57.0 |
| 43 | $CH_3$ | 2-Cl, 6-F | 4-$C_{13}H_{27}$ | 43.0–47.0 |
| 44 | $CH_3$ | 2,6-$F_2$ | 4-$C_{13}H_{27}$ | 37.0–40.0 |
| 45 | $CH_3$ | 2,6-$Cl_2$ | 4-$C_{13}H_{27}$ | 52.0–55.0 |
| 46 | $CH_3$ | 2-Cl | 4-$C_{14}H_{29}$ | 66.0–67.5 |
| 47 | $CH_3$ | 2-Cl, 6-F | 4-$C_{14}H_{29}$ | 56.0–58.0 |
| 48 | $CH_3$ | 2,6-$F_2$ | 4-$C_{14}H_{29}$ | 61.0–62.5 |
| 49 | $CH_3$ | 2,6-$Cl_2$ | 4-$C_{14}H_{29}$ | 47.0–49.0 |
| 50 | $CH_3$ | 2-Cl | 4-$C_{15}H_{31}$ | 62.0–65.0 |
| 51 | $CH_3$ | 2-Cl, 6-F | 4-$C_{15}H_{31}$ | 61.0–63.0 |
| 52 | $CH_3$ | 2,6-$F_2$ | 4-$C_{15}H_{31}$ | 54.0–56.0 |

TABLE 3

| Compound No. | $R^1$ | Xn | Y | Melting point (°C.) or refractive index ($n_D^{20}$) |
|---|---|---|---|---|
| 53 | $CH_3$ | 2,6-$Cl_2$ | 4-$C_{15}H_{31}$ | 61.5–64.0 |
| 54 | $CH_3$ | 2-Cl | 4-$C_{16}H_{33}$ | 70.0–73.0 |
| 55 | $CH_3$ | 2-Cl, 6-F | 4-$C_{16}H_{33}$ | 65.0–67.0 |
| 56 | $CH_3$ | 2,6-$F_2$ | 4-$C_{16}H_{33}$ | 55.0–57.0 |
| 57 | $CH_3$ | 2,6-$Cl_2$ | 4-$C_{16}H_{33}$ | 69.5–71.0 |
| 58 | $CH_3$ | 2-Cl | 4-$C_{17}H_{35}$ | |
| 59 | $CH_3$ | 2-Cl, 6-F | 4-$C_{17}H_{35}$ | |
| 60 | $CH_3$ | 2,6-$F_2$ | 4-$C_{17}H_{35}$ | |
| 61 | $CH_3$ | 2-Cl | 4-$C_{18}H_{37}$ | |
| 62 | $CH_3$ | 2-Cl, 6-F | 4-$C_{18}H_{37}$ | |
| 63 | $CH_3$ | 2,6-$F_2$ | 4-$C_{18}H_{37}$ | |
| 64 | $C_2H_5$ | 2-Cl, 6-F | 4-$C_{12}H_{25}$ | 43.0–45.0 |
| 65 | $CH(CH_3)_2$ | 2-Cl | 4-$C_{12}H_{25}$ | |
| 66 | $CH(CH_3)_2$ | 2-Cl, 6-F | 4-$C_{12}H_{25}$ | 63.0–66.0 |
| 67 | $CH_3$ | 2-Cl | 4-$CH_2CH_2CH_2CH_2CH(CH_3)_2$ | 64.0–67.0 |
| 68 | $CH_3$ | 2-Cl, 6-F | 4-$CH_2CH_2CH_2CH_2CH(CH_3)_2$ | 1.5614 |
| 69 | $CH_3$ | 2,6-$F_2$ | 4-$CH_2CH_2CH_2CH_2CH(CH_3)_2$ | 1.5578 |
| 70 | $CH_3$ | 2-Cl | 4-$CH_2CH_2CH_2CH(C_2H_5)CH_3$ | 1.5935 |
| 71 | $CH_3$ | 2-Cl, 6-F | 4-$CH_2CH_2CH_2CH(C_2H_5)CH_3$ | 1.5759 |
| 72 | $CH_3$ | 2-Cl | 4-$CH_2CH_2CH(CH_3)CH_2CH_2CH_3$ | 1.5879 |
| 73 | $CH_3$ | 2-Cl, 6-F | 4-$CH_2CH_2CH(CH_3)CH_2CH_2CH_3$ | 1.5693 |
| 74 | $CH_3$ | 2-Cl | 4-$CH_2CH_2CH_2C(CH_3)_3$ | |
| 75 | $CH_3$ | 2-Cl, 6-F | 4-$CH_2CH_2CH_2C(CH_3)_3$ | |
| 76 | $CH_3$ | 2,6-$F_2$ | 4-$CH_2CH_2CH_2C(CH_3)_3$ | |
| 77 | $CH_3$ | 2-Cl | 4-$OC_8H_{17}$ | 58.0–59.5 |
| 78 | $CH_3$ | 2-Cl | 4-$O(CH_2)_4CH(CH_3)_2$ | |
| 79 | $CH_3$ | 2-Cl, 6-F | 4-$O(CH_2)_4CH(CH_3)_2$ | |

TABLE 4

| Compound No. | $R^1$ | Xn | Y | Melting point (°C.) or refractive index ($n_D^{20}$) |
|---|---|---|---|---|
| 80 | $CH_3$ | 2-Cl | 4-$OCH_2$-cyclohexyl | 83.0–86.0 |
| 81 | $CH_3$ | 2-Cl, 6-F | 4-$OCH_2$-cyclohexyl | 83.0–85.0 |
| 82 | $CH_3$ | 2-Cl | 4-$OC_{10}H_{21}$ | 67.5–69.0 |
| 83 | $CH_3$ | 2-Cl, 6-F | 4-$OC_{10}H_{21}$ | 55.0–57.0 |
| 84 | $CH_3$ | 2,6-$F_2$ | 4-$OC_{10}H_{21}$ | 1.5399 |
| 85 | $CH_3$ | 2,6-$Cl_2$ | 4-$OC_{10}H_{21}$ | 60.0–64.0 |
| 86 | $CH_3$ | 2-Cl | 4-$OC_{12}H_{25}$ | 73.5–75.0 |
| 87 | $CH_3$ | 2-Cl, 6-F | 4-$OC_{12}H_{25}$ | 59.0–61.0 |
| 88 | $CH_3$ | 2-Cl | 4-$SC_8H_{17}$ | |
| 89 | $CH_3$ | 2-Cl, 6-F | 4-$SC_8H_{17}$ | |
| 90 | $CH_3$ | 2-Cl | 4-$SOC_8H_{17}$ | |
| 91 | $CH_3$ | 2-Cl | 4-$SO_2C_8H_{17}$ | |
| 92 | $CH_3$ | 2-Cl | 4-$OCH_2CH_2OCH_3$ | |
| 93 | $CH_3$ | 2-Cl | 4-$CH_2OC_4H_9$ | 1.5850 |
| 94 | $CH_3$ | 2-Cl | 4-$CH_2OC_{10}H_{21}$ | |
| 95 | $CH_3$ | 2-Cl, 6-F | 4-$CH_2OC_{10}H_{21}$ | |
| 96 | $CH_3$ | 2-Cl, 6-F | 4-$CH_2SC_3H_7$ | 1.6023 |
| 97 | $CH_3$ | 2-Cl | 4-CH=$CHCH_3$ | 1.6410 |
| 98 | $CH_3$ | 2-Cl | 4-CH=$CHC_{10}H_{21}$ | |
| 99 | $CH_3$ | 2-Cl, 6-F | 4-CH=$CHC_{10}H_{21}$ | |
| 100 | $CH_3$ | 2-Cl | 4-C≡$CCH_3$ | 93.5–95.0 |
| 101 | $CH_3$ | 2-Cl, 6-F | 4-C≡$CCH_3$ | 124.0–126.5 |
| 102 | $CH_3$ | 2-Cl | 2-C≡$CC_2H_5$ | 1.6249 |
| 103 | $CH_3$ | 2-Cl | 4-C≡$CC_2H_5$ | 1.6478 |
| 104 | $CH_3$ | 2,6-$F_2$ | 4-C≡$CC_2H_5$ | 1.6158 |

TABLE 5

| Compound No. | $R^1$ | Xn | Y | Melting point (°C.) or refractive index ($n_D^{20}$) |
|---|---|---|---|---|
| 105 | $CH_3$ | 2-Cl, 6-F | 4-C≡$CC_2H_5$ | 1.6244 |
| 106 | $CH_3$ | 2-Cl | 3-C≡$CC_3H_7$ | 1.6265 |
| 107 | $CH_3$ | 2-Cl | 4-C≡$CC_3H_7$ | 1.5380 |

TABLE 5-continued

| Compound No. | $R^1$ | Xn | Y | Melting point (°C.) or refractive index ($n_D^{20}$) |
|---|---|---|---|---|
| 108 | $CH_3$ | 2,6-F2 | 4-C≡$CC_3H_7$ | 1.6018 |
| 109 | $CH_3$ | 2-Cl, 6-F | 4-C≡$CC_3H_7$ | 1.6175 |
| 110 | $CH_3$ | 2-Cl | 4-C≡$CCH_2CH(CH_3)_2$ | 82.0–84.0 |
| 111 | $CH_3$ | 2-Cl | 3-C≡$CC_4H_9$ | 1.6191 |
| 112 | $CH_3$ | 2-Cl, 6-F | 3-C≡$CC_4H_9$ | 1.6121 |
| 113 | $CH_3$ | 2-Cl | 4-C≡$CC_4H_9$ | 1.6273 |
| 114 | $CH_3$ | 2-Cl, 6-F | 4-C≡$CC_4H_9$ | 1.6110 |
| 115 | $CH_3$ | 2,6-$F_2$ | 4-C≡$CC_4H_9$ | |
| 116 | $CH_3$ | 2,6-$Cl_2$ | 4-C≡$CC_4H_9$ | |
| 117 | $CH_3$ | 2-Cl | 3-C≡$CC_5H_{11}$ | 1.6010 |
| 118 | $CH_3$ | 2-Cl, 6-F | 3-C≡$CC_5H_{11}$ | 1.5947 |
| 119 | $CH_3$ | 2-Cl | 4-C≡$CC_5H_{11}$ | 1.6224 |
| 120 | $CH_3$ | 2-Cl, 6-F | 4-C≡$CC_5H_{11}$ | 1.6052 |
| 121 | $CH_3$ | 2,6-$F_2$ | 4-C≡$CC_5H_{11}$ | |
| 122 | $CH_3$ | 2,6-$Cl_2$ | 4-C≡$CC_5H_{11}$ | |
| 123 | $CH_3$ | 2-Cl, 6-F | 4-C≡$CC_6H_{13}$ | |
| 124 | $CH_3$ | 2,6-$F_2$ | 4-C≡$CC_6H_{13}$ | |
| 125 | $CH_3$ | 2,6-$Cl_2$ | 4-C≡$CC_6H_{13}$ | |
| 126 | $CH_3$ | 2-Cl | 4-C≡$CC_8H_{17}$ | 1.5852 |
| 127 | $CH_3$ | 2-Cl, 6-F | 4-C≡$CC_8H_{17}$ | 60.5–64.0 |
| 128 | $CH_3$ | 2-Cl | 4-(cyclohexyl) | 79.5–82.0 |
| 129 | $CH_3$ | 2-Cl | 3-$CH_2$-(cyclohexyl) | |

TABLE 6

| Compound No. | $R^1$ | Xn | Y | Melting point (°C.) or refractive index ($n_D^{20}$) |
|---|---|---|---|---|
| 130 | $CH_3$ | 2-Cl | 4-$CH_2CH_2$-(cyclopentyl) | 116.0–118.0 |
| 131 | $CH_3$ | 2-Cl, 6-F | 4-$CH_2CH_2$-(cyclopentyl) | 88.5–90.0 |
| 132 | $CH_3$ | 2-Cl | 4-$CH_2CH_2$-(cyclohexyl) | |
| 133 | $CH_3$ | 2-Cl, 6-F | 4-$CH_2CH_2$-(cyclohexyl) | |
| 134 | $CH_3$ | 2-Cl | 4-$(CH_2)_3$-(cyclopentyl) | 65.0–69.0 |
| 135 | $CH_3$ | 2-Cl, 6-F | 4-$(CH_2)_3$-(cyclopentyl) | 53.0–57.0 |
| 136 | $CH_3$ | 2-Cl | 4-$(CH_2)_3$-(cyclohexyl) | 118.0–121.0 |

TABLE 6-continued

| Compound No. | R¹ | Xn | Y | Melting point (°C.) or refractive index ($n_D^{20}$) |
|---|---|---|---|---|
| 137 | CH₃ | 2-Cl, 6-F | 4-(CH₂)₃-cyclohexyl | 100.0–103.0 |
| 138 | CH₃ | 2-Cl | 4-CH=CH-cyclohexyl | |
| 139 | CH₃ | 2-Cl | 4-C≡C-cyclohexyl | |
| 140 | CH₃ | 2-Cl, 6-F | 4-C≡C-cyclohexyl | |
| 141 | CH₃ | 2-Cl | 4-CH₂CH₂—Si(CH₃)₃ | 79.0–81.0 |
| 142 | CH₃ | 2-Cl, 6-F | 4-CH₂CH₂—Si(CH₃)₃ | 1.5728 |
| 143 | CH₃ | 2-Cl | 4-O—CH₂—Si(CH₃)₃ | 55.0–57.0 |
| 144 | CH₃ | 2-Cl, 6-F | 4-O—CH₂—Si(CH₃)₃ | 1.5730 |
| 145 | C₂H₅ | 2-Cl, 6-F | 4-C₁₆H₃₃ | 56.0–59.0 |
| 146 | CH₃ | 2,6-F₂ | 4-CH₂CH₂CH₂-cyclopentyl | not measurable |
| 147 | CH₃ | 2-Cl | 4-C≡C—CH(CH₃)CH₂CH₂CH₃ | 1.6171 |
| 148 | CH₃ | 2-Cl | 3-C₈H₁₇ | 1.5810 |
| 149 | CH₃ | 2-Cl, 6-F | 3-C₈H₁₇ | 1.5586 |
| 150 | CH₃ | 2-Cl | 3-CH₂CH₂C(CH₃)₃ | 1.5803 |
| 151 | CH₃ | 2-Cl, 6-F | 3-CH₂CH₂C(CH₃)₃ | 1.5499 |
| 152 | CH₃ | 2-Cl | 3-OC₈H₁₇ | 1.5789 |
| 153 | CH₃ | 2-Cl, 6-F | 3-OC₈H₁₇ | 1.559 |

TABLE 7

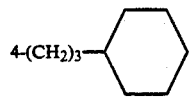

| Compound No. | R¹ | Xn | Substitution position | A | R²m | Melting point (°C.) or refractive index ($n_D^{20}$) |
|---|---|---|---|---|---|---|
| 154 | CH₃ | 2-Cl | 4- | — | H | 152.0–154.5 |
| 155 | CH₃ | 2,6-F₂ | 4- | — | 4-C₃H₇ | 112.0–116.0 |
| 156 | CH₃ | 2-Cl | 4- | — | 4-C₃H₇ | 111.5–114.0 |
| 157 | CH₃ | 2-Cl, 6-F | 4- | — | 4-C₃H₇ | 158.0–160.5 |
| 158 | CH₃ | 2-Cl | 4- | — | 4-C₆H₁₃ | 112.0–114.0 |
| 159 | CH₃ | 2-Cl, 6-F | 4- | — | 4-C₆H₁₃ | 93.0–95.0 |
| 160 | CH₃ | 2,6-F₂ | 4- | — | 4-C₆H₁₃ | 96.0–98.0 |
| 161 | CH₃ | 2,6-Cl₂ | 4- | — | 4-C₆H₁₃ | 96.0–97.5 |
| 162 | CH₃ | 2-Cl | 4- | — | 4-Cl | 142.0–143.0 |
| 163 | CH₃ | 2-Cl | 4- | — | 4-OCH₃ | 137.0–141.0 |
| 164 | CH₃ | 2-Cl | 4- | — | 3-CH₃ | 137.0–139.0 |
| 165 | CH₃ | 2-Cl | 4- | CH₂ | H | 68.0–71.0 |
| 166 | CH₃ | 2-Cl, 6-F | 4- | CH₂ | H | 1.6248 |
| 167 | CH₃ | 2-Cl | 4- | CH₂ | 4-Cl | |
| 168 | CH₃ | 2-Cl, 6-F | 4- | CH₂ | 4-Cl | |
| 169 | CH₃ | 2-Cl | 4- | CH₂ | 4-C₄H₉ | |
| 170 | CH₃ | 2-Cl, 6-F | 4- | CH₂ | 4-C₄H₉ | |
| 171 | CH₃ | 2-Cl | 4- | CH₂CH₂ | H | 68.0–69.0 |
| 172 | CH₃ | 2-Cl, 6-F | 4- | CH₂CH₂ | H | 160.0–162.0 |
| 173 | CH₃ | 2-Cl | 4- | CH₂O | H | 99.0–102.0 |
| 174 | CH₃ | 2-Cl, 6-F | 4- | CH₂O | H | 103.0–106.0 |

TABLE 7-continued

| Compound No. | R[1] | Xn | Substitution position | A | R[2]m | Melting point (°C.) or refractive index ($n_D^{20}$) |
|---|---|---|---|---|---|---|
| 175 | CH$_3$ | 2-Cl | 4— | OCH$_2$ | H | 83.0–87.0 |
| 176 | CH$_3$ | 2-Cl, 6-F | 4— | OCH$_2$ | H | 143.0–153.0 |

TABLE 8

| Compound No. | R[1] | Xn | Substitution position | A | R[2]m | Melting point (°C.) or refractive index ($n_D^{20}$) |
|---|---|---|---|---|---|---|
| 177 | CH$_3$ | 2-Cl | 4— | CH$_2$OCH$_2$ | H | |
| 178 | CH$_3$ | 2-Cl, 6-F | 4— | CH$_2$OCH$_2$ | H | |
| 179 | CH$_3$ | 2-Cl | 3— | O | H | 1.6354 |
| 180 | CH$_3$ | 2-Cl | 4— | O | H | 106.0–108.0 |
| 181 | CH$_3$ | 2-Cl, 6-F | 4— | O | H | 165.0–168.0 |
| 182 | CH$_3$ | 2,6-F$_2$ | 4— | O | H | 85.0–89.0 |
| 183 | CH$_3$ | 2-Cl | 4— | O | 4-CH$_3$ | not measurable |
| 184 | CH$_3$ | 2-Cl, 6-F | 4— | O | 4-CH$_3$ | not measurable |
| 185 | CH$_3$ | 2-Cl | 4— | O | 4-C$_4$H$_9$ | |
| 186 | CH$_3$ | 2-Cl, 6-F | 4— | O | 4-C$_4$H$_9$ | |
| 187 | CH$_3$ | 2-Cl | 4— | O | 2-Cl | |
| 188 | CH$_3$ | 2-Cl, 6-F | 4— | O | 2-Cl | |
| 189 | CH$_3$ | 2-Cl | 4— | O | 2-Cl, 4-CF$_3$ | |
| 190 | CH$_3$ | 2-Cl, 6-F | 4— | O | 2-Cl, 4-CF$_3$ | |
| 191 | CH$_3$ | 2-Cl | 4— | — | 4-CH$_3$ | 151.0–154.0 |
| 192 | CH$_3$ | 2-Cl, 6-F | 4— | — | 4-CH$_3$ | 207.0–211.0 |
| 193 | CH$_3$ | 2-Cl | 4— | — | 4-OCF$_3$ | 119.0–122.0 |
| 194 | CH$_3$ | 2-Cl, 6-F | 4— | — | 4-OCF$_3$ | 114.0–116.0 |
| 195 | CH$_3$ | 2-Cl | 4— | — | 4-CF$_3$ | 155.0–159.0 |
| 196 | CH$_3$ | 2-Cl, 6-F | 4— | — | 4-CF$_3$ | 146.0–149.0 |
| 197 | CH$_3$ | 2-Cl | 4— | — | 3,4-Cl$_{12}$ | |
| 198 | CH$_3$ | 2-Cl, 6-F | 4— | — | 3,4-Cl$_{12}$ | |
| 199 | CH$_3$ | 2-Cl | 4— | — | 2,4-Cl$_{12}$ | |
| 200 | CH$_3$ | 2-Cl, 6-F | 4— | — | 2,4-Cl$_{12}$ | |
| 201 | CH$_3$ | 2-Cl | 4— | CH$_2$O | 4-CH$_3$ | 135.0–138.0 |
| 202 | CH$_3$ | 2-Cl, 6-F | 4— | CH$_2$O | 4-CH$_3$ | 149.0–152.0 |
| 203 | CH$_3$ | 2-Cl | 4— | CH$_2$O | 4-C$_4$H$_9$ | |
| 204 | CH$_3$ | 2-Cl, 6-F | 4— | CH$_2$O | 4-C$_4$H$_9$ | |
| 205 | CH$_3$ | 2-Cl | 4— | OCH$_2$ | 4-CH$_3$ | 108.0–110.0 |
| 206 | CH$_3$ | 2-Cl, 6-F | 4— | OCH$_2$ | 4-CH$_3$ | 150.0–155.0 |
| 207 | CH$_3$ | 2-Cl | 4— | OCH$_2$ | 2,3,4,5,6-F$_5$ | |
| 208 | CH$_3$ | 2-Cl, 6-F | 4— | OCH$_2$ | 2,3,4,5,6-F$_5$ | |
| 209 | CH$_3$ | 2-Cl | 4— | O | 4-C$_8$H$_{15}$ | 1.6060 |

TABLE 9

| Compound No. | R[1] | Xn | Substitution position | A | R[2]m | Melting point (°C.) or refractive index ($n_D^{20}$) |
|---|---|---|---|---|---|---|
| 210 | CH$_3$ | 2-Cl, 6-F | 4— | O | 4-C$_6$H$_{13}$ | 1.5891 |
| 211 | CH$_3$ | 2-Cl | 4— | O | 3,4-Cl$_2$ | 115.0–118.0 |
| 212 | CH$_3$ | 2-Cl, 6-F | 4— | O | 3,4-Cl$_2$ | 103.0–106.0 |
| 213 | CH$_3$ | 2-Cl | 4— | O | 2,4-Cl$_2$ | not measurable |
| 214 | CH$_3$ | 2-Cl, 6-F | 4— | O | 2,4-Cl$_2$ | not measurable |
| 215 | CH$_3$ | 2-Cl, 6-F | 4— | — | 4-OCH$_3$ | 191.0–192.0 |
| 216 | CH$_3$ | 2-Cl | 4— | — | 4-OC$_4$H$_9$ | 118.0–121.0 |
| 217 | CH$_3$ | 2-Cl, 6-F | 4— | — | 4-OC$_4$H$_9$ | 141.0–144.0 |
| 218 | CH$_3$ | 2-Cl, 6-F | 4— | — | 3-CH$_3$ | 131.0–134.0 |
| 219 | CH$_3$ | 2-Cl, 6-F | 4— | — | 4-Cl | 105.0–107.0 |
| 220 | CH$_3$ | 2-Cl | 4— | CH$_2$CH$_2$ | 4-CH$_3$ | 95.0–97.0 |
| 221 | CH$_3$ | 2-Cl, 6-F | 4— | CH$_2$CH$_2$ | 4-CH$_3$ | 188.0–192.0 |
| 222 | CH$_3$ | 2-Cl | 4— | O | 3,5-Cl$_2$ | 105.0–108.0 |
| 223 | CH$_3$ | 2-Cl | 4— | O | 3,5-Cl$_2$ | 121.0–123.0 |
| 224 | CH$_3$ | 2-Cl, 6-F | 4— | O | 4-Cl | not measurable |

TABLE 10

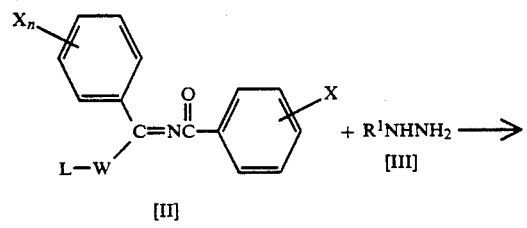

| Compound No. | R¹ | Xn | Substitution position | A | R²m | Melting point (°C.) or refractive index ($n_D^{20}$) |
|---|---|---|---|---|---|---|
| 225 | $CH_3$ | 2-Cl | 4- | O | H | |
| 226 | $CH_3$ | 2-Cl, 6-F | 4- | O | H | |
| 227 | $CH_3$ | 2-Cl | 4- | O | 5-$CF_3$ | not measurable |
| 228 | $CH_3$ | 2-Cl, 6-F | 4- | O | 5-$CF_3$ | 107.0–109.0 |
| 229 | $CH_3$ | 2-Cl | 4- | O | 3-Cl, 5-$CF_3$ | not measurable |
| 230 | $CH_3$ | 2-Cl, 6-F | 4- | O | 3-Cl, 5-$CF_3$ | not measurable |
| 231 | $CH_3$ | 2-Cl | 4- | S | 3-Cl, 5-$CF_3$ | |
| 232 | $CH_3$ | 2-Cl | 4- | $CH_2O$ | H | |
| 233 | $CH_3$ | 2-Cl, 6-F | 4- | $CH_2O$ | H | |

The compounds according to the invention can be produced by the following methods. However, it is not intended to restrict the invention to these methods.

Production Method A

The compounds of the general formula [I] according to the invention can be obtained by reacting an alkyl N-acyl(thio) imidate derivative of a general formula [II] with a hydrazine derivative of a general formula [III] in an inert solvent according to the following reaction formula (1):

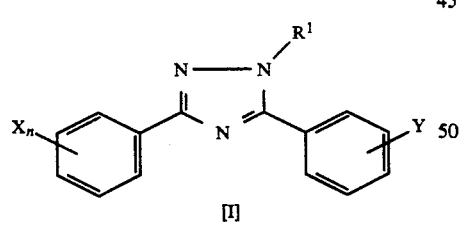

(wherein W is a sulfur atom or an oxygen atom, L is an alkyl group having a carbon number of 1–4 and R¹, X, n and Y have the same meaning as mentioned above).

As the solvent, use may be made of any solvent not obstruction the reaction, which includes, for example, an alcohol such as methanol, ethanol or the like; an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a nitrile such as acetonitrile or the like; an aprotic polar solvent such as N,N-dimethylformamide, N,N-dimethylacetamide, dimethylsulfoxide or the like; water and a mixture thereof.

In general, the compound of the general formula [III] is used in an amount of 1.0–5.0 moles per 1 mole of the compound of the general formula [II].

The reaction temperature is optional within a range of 0° C. to a boiling point of the solvent, but is preferably 0° C.–50° C.. The reaction time is dependent upon the kind of compounds used, but is usually 1–72 hours.

A concrete example of this reaction is disclosed, for example, in Synthesis, page 483 (1983).

The compound of the general formula [II] as a starting material can be produced by the following method.

Production Method B

The compound of the general formula [II] can be obtained by reacting compounds of general formulae [IV] and [V] in an inert solvent in the presence of a base according to the following reaction formula (2):

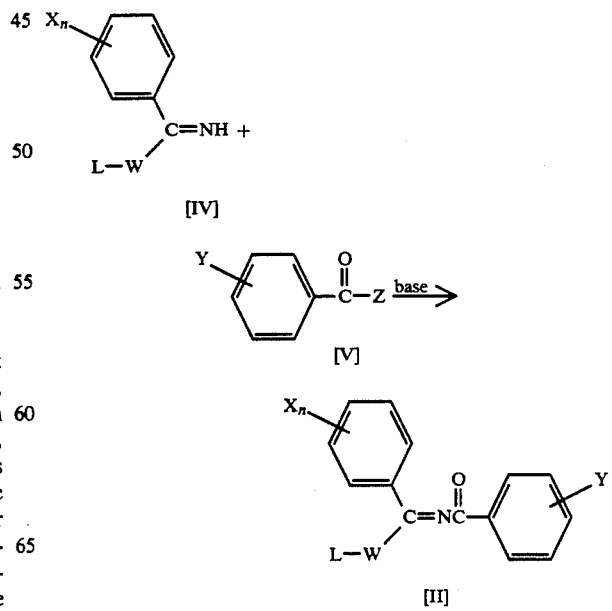

(wherein a derivative of the general formula [IV] may be an acid addition salt (e.g. a salt with boron tetra-fluoride, hydrogen chloride, hydrogen bromide, hydrogen iodide or the like), Z is a halogen atom, and L, W, X, n and Y have the same meaning as mentioned above).

As the base, use may be made of an inorganic base such as sodium carbonate, potassium carbonate, sodium hydrogen carbonate, sodium hydroxide, potassium hydroxide or the like; and an organic base such as diethylamine, triethylamine, diisopropylethylamine, pyridine, 4-N,N-dimethylamino pyridine or the like.

As the solvent, use may be made of a ketone such as acetone, methyl ethyl ketone or the like; an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a nitrile such as acetonitrile or the like; an aprotic polar solvent such as N,N-dimethylformamide, N,N-dimethylacetamide, dimethylsulfoxide or the like; and a mixture thereof.

In general, the compound of the general formula [V] is used in an amount of 0.8-1.3 moles per 1 mole of the compound of the general formula [IV]. The amount of the base used is 1.0-2.0 moles per 1 mole of the compound of the general formula [IV].

The reaction time is dependent upon the kind of the compounds used, but is usually within a range of 1-24 hours. The reaction temperature is within a range of 0° C. to a boiling point of the solvent.

Production Method C

The compound of the general formula [I] according to the invention can be obtained by reacting an N-(phenylsulfonyl) benzohydrazonoyl chloride derivative of a general formula [VI] with a benzonitrile derivative of a general formula [VII] in an inert solvent in the presence of Lewis acid according to the following reaction formula (3):

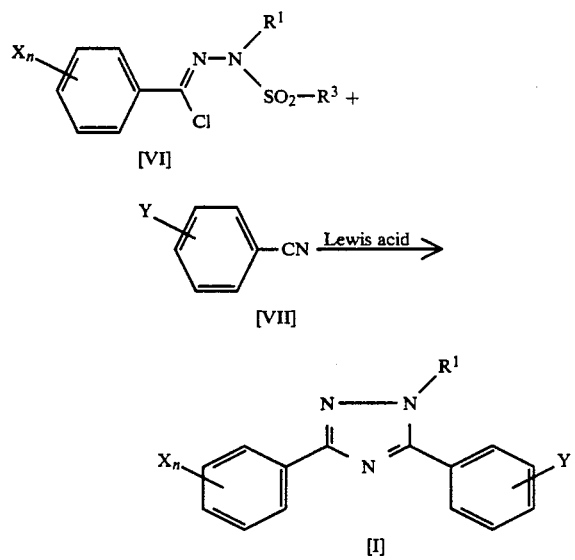

(wherein $R^1$, X, n and Y have the same meaning as mentioned above, and $R^3$ is benzene or benzene substituted with an alkyl group having a carbon number of 1-4).

As the solvent, use may be made of any solvent not obstruction the reaction, which includes, for example, an ether such as diethyl ether, tetrahydrofuran, dioxane, diglyme or the like; an aromatic hydrocarbon such as benzene, toluene, chlorobenzene, dichlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a non-protonic polar solvent such as nitrobenzene, N,N-dimethylformamide, N,N-dimethylacetamide, dimethylsulfoxide or the like; and a mixture thereof.

As the Lewis acid, use may be made of aluminum bromide, aluminium chloride, ferric chloride, boron trifluoride, titanium tetrachloride and the like.

In general, the amount of the compound of the general formula [VII] used is 1.0-2.0 moles per 1 mole of the compound of the general formula [VI], and the amount of Lewis acid used is 1.0-2.0 moles per 1 mole of the compound of the general formula [VI].

The reaction temperature is optionally within a range of 0° C. to a boiling point of the solvent, but is preferably within a range of 50°-180° C. The reaction time is dependent upon the kind of the compounds used, but is usually within a range of 15 minutes to 8 hours.

A concrete example of this reaction is disclosed, for example, in Bulletin of the Chemical Society of Japan, vol. 56, pages 547-548 (1983).

Production Method D

The compound of the general formula [I] according to the invention can be obtained by reacting an N-(phenylsulfonyl) benzamidrazone derivative of a general formula [VIII] with a benzoylhalide derivative of the general formula [V] in the absence of a solvent or in an inert solvent according to the following reaction formula (4):

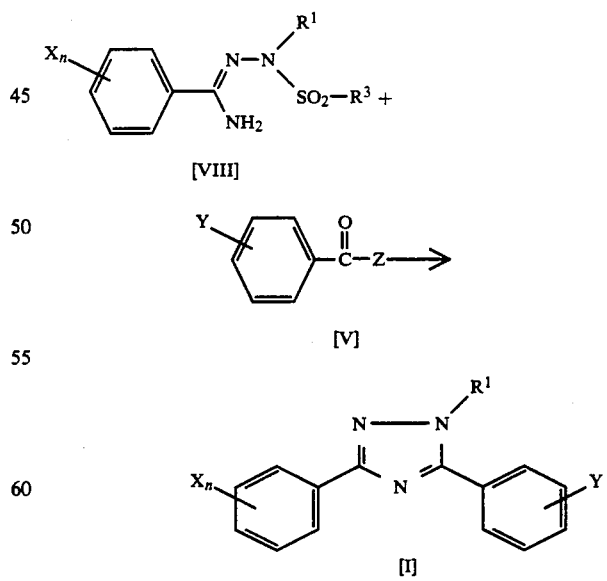

(wherein $R^1$, $R^3$, X, n, Y and Z have the same meaning as mentioned above).

As the solvent, use may be made of any solvent not obstruction the reaction, which includes, for example, an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; an aprotic polar solvent such as N,N-dimethylformamide, N,N-dimethylacetamide, dimethylsulfoxide, 1-methyl-2-pyrolidinone or the like; and a mixture thereof.

In general, the amount of the compound of the general formula [V] used is 1.0–2.0 moles per 1 mole of the compound of the general formula [VIII].

The reaction temperature is optionally within a range of 0° C. to a boiling point of the solvent, but is preferably within a range of 50°–250° C. The reaction time is dependent upon the kind of the compounds used, but is usually within a range of 30 minutes to 5 hours.

A concrete example of this reaction is disclosed, for example, in Bulletin of the Chemical Society of Japan, vol. 56, page 548 (1983).

The compound of the general formula [VIII] as a starting material can be produced by the following method.

Production Method E

The compound of the general formula [VIII] can be obtained by reacting the compound of the general formula [VI] with ammonia gas in an inert solvent according to the following reaction formula (5):

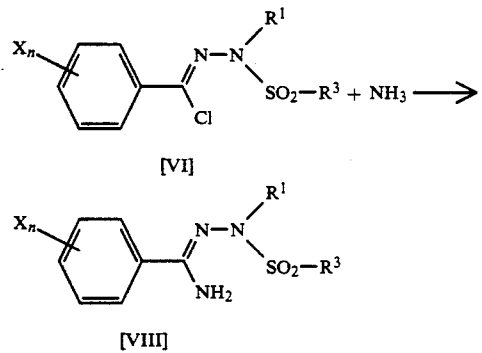

[VIII]

(wherein $R^1$, $R^3$, X and n have the same meaning as mentioned above).

As the solvent, use may be made of any solvent not obstruction the reaction, which includes, for example, an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride, diclorobenzene or the like; an aprotic polar solvent such as N,N-dimethylformamide, N,N-dimethylacetamide, dimethylsulfoxide or the like; and a mixture thereof.

In general, the amount of ammonia gas used is 5.0–10.0 moles per 1 mole of the compound of the general formula [VI].

The reaction temperature is optionally within a range of 0° C. to a boiling point of the solvent, but is preferably within a range of 20°–150° C. The reaction time is dependent upon the kind of the compounds used, but is usually within a range of 1–24 hours.

A concrete example of this reaction is disclosed, for example, in Bulletin of the Chemical Society of Japan, vol. 56, pages 545–548 (1983).

The invention will be described concretely with reference to the following production examples, formulation examples and applications.

PRODUCTION EXAMPLE 1

3-(2-chloro-6-fluorophenyl)-1-methyl-5-(4-octylphenyl)-1H-1,2,4-triazole (Compound No. 15)

In 100 ml of toluene were dissolved 2.20 g of ethyl 2 chloro-6-fluorobenzimidate and 1.10 g of triethylamine, to which was added dropwise 2.53 g of 4-octylbenzoyl chloride within a temperature range of 5°–10° C. with stirring and then stirred at room temperature for 1 hour and further refluxed under heating for 2 hours. After the cooling to room temperature, the resulting reaction solution was added with 100 ml of toluene, washed with a diluted hydrochloric acid and further with a saline solution, and thereafter the resulting toluene layer was dried over anhydrous magnesium sulfate.

The toluene layer was added with 3.00 g of monomethylhydrazine and stirred at room temperature for 8 hours. After the completion of the reaction, the reaction mixture was washed with a diluted hydrochloric acid solution and further with a saturated saline solution, dried over anhydrous magnesium sulfate and concentrated under a reduced pressure. The resulting concentrate was purified through a chromatography of silica gel column using a mixed solution of hexane and ethyl acetate as a developing solvent to obtain 1.34 g of the given compound ($n_D^{20}$ = 1.5652).

| NMR data (60 MHz, CDCl$_3$ solvent, δ value) | |
|---|---|
| 0.77 | (3H, t) |
| 1.00–1.79 | (12H, m) |
| 2.57 | (2H, t) |
| 3.95 | (3H, s) |
| 6.83–7.67 | (7H, m) |

PRODUCTION EXAMPLE 2

3-(2-chlorophenyl)-1-methyl-5-[4-(6-methylhexyl)-phenyl]-1H-1,2,4-triazole (Compound No. 67)

A mixture of 2.06 g of N-methyl-N-phenylsulfonyl-2-chlorobenzohydrazonoyl chloride, 1.30 g of 4-(6-methylhexyl) benzonitrile, 0.93 g of anhydrous aluminum chloride and 5 ml of o-dichlorobenzene was stirred in an oil bath at a temperature of 140° C. for 30 minutes. After the cooling, the resulting solution was dissolved in 200 ml of chloroform, washed with diluted hydrochloric acid solution, diluted sodium hydroxide aqueous solution and saline water in this order, dried over anhydrous magnesium sulfate and concentrated under a reduced pressure. The resulting concentrate was purified through a chromatography of silica gel column using a mixed solution of hexane and ethyl acetate as a developing solvent to obtain 1.52 g of the given compound (melting point: 64.0°–67.0° C.).

| NMR data (60 MHz, CDCl$_3$ solvent, δ value) | |
|---|---|
| 0.86 | (6H, d) |
| 1.15–1.80 | (7H, m) |
| 2.67 | (2H, t) |
| 4.00 | (3H, s) |

| 7.17–8.00 | (8H, m) |

PRODUCTION EXAMPLE 3

3-(2-chlorophenyl)-1-methyl-5-(4-tridecylphenyl)-1H-1,2,4-triazole (Compound No. 42)

A mixture of 0.82 g of N-methyl-N-phenylsulfonyl-2-chlorobenzohydrazonoyl chloride, 0.70 g of 4-tridecylbenzonitrile, 0.4 g of anhydrous aluminium chloride and 3 ml of o-dichlorobenzene was stirred in an oil bath at a temperature of 140° C. for 30 minutes. After the cooling, the resulting solution was dissolved in 100 ml of chloroform, washed with diluted hydrochloric acid solution, diluted sodium hydroxide solution and saline water in this order, dried over anhydrous magnesium sulfate and concentrated under a reduced pressure. The resulting concentrate was purified through a chromatography of silica gel column using a mixed solution of hexane and ethyl acetate as a developing solvent to obtain 0.70 g of the given compound (melting point: 55.0°–57.0° C.).

| NMR data (60 MHz, CDCl$_3$ solvent, δ value) | |
|---|---|
| 0.67–1.80 | (25H, m) |
| 2.67 | (2H, t) |
| 4.00 | (3H, s) |
| 7.16–8.03 | (8H, m) |

PRODUCTION EXAMPLE 4

3(2-chlorophenyl)-1-methyl-5-(4-pentadecylphenyl)-1H-1,2,4-triazole (Compound No. 50)

A mixture of 3.24 g of N-methyl-N-phenylsulfonyl-2-chlorobenzamidrazone and 3.50 g of 4-pentadecylbenzoyl chloride was stirred in an oil bath at a temperature of 170°–180° C. for 4 hours. After the cooling, the resulting solution was added with water and extracted with ethyl acetate (200 ml×2) and the extracted organic layer was washed with saline water, dried over anhydrous magnesium sulfate and concentrated under a reduced pressure. The resulting concentrate was purified through a chromatography of silica gel column using a mixed solution of hexane and ethyl acetate as a developing solvent and washed with n-hexane to obtain 0.34 g of the given compound (melting point: 62.0°–65.0° C.).

| NMR data (60 MHz, CDCl$_3$ solvent, δ value) | |
|---|---|
| 0.77–1.73 | (29H, m) |
| 1.67 | (2H, m) |
| 4.00 | (3H, s) |
| 7.17–7.97 | (8H, m) |

PRODUCTION EXAMPLE 5

5-(4-decyloxyphenyl)-3-(2,6-dichlorophenyl)-1-methyl-1H-1,2,4-triazole (Compound No. 85)

A mixture of 1.10 g of N-methyl-N-phenylsulfonyl-2,6-dichlorobenzohydrazonoyl chloride, 0.70 g of 4-decyloxybenzonitrile, 0.4 g of anhydrous aluminium chloride and 3 ml of o-dichlorobenzene was stirred in an oil bath at a temperature of 140° C. for 30 minutes. After the cooling, the resulting solution was dissolved in 100 ml of chloroform, washed with diluted hydrochloric acid solution, diluted sodium hydroxide solution and saline water in this order, dried over anhydrous magnesium sulfate and concentrated under a reduced pressure. The resulting concentrate was purified through a chromatography of silica gel column using a mixed solution of hexane and ethyl acetate as a developing solvent to obtain 0.40 g of the given compound (melting point: 60.0°–64.0° C.).

| NMR data (60 MHz, CDCl$_3$ solvent, δ value) | |
|---|---|
| 0.77–1.90 | (19H, m) |
| 3.98 | (2H, t) |
| 4.04 | (3H, s) |
| 6.88–7.73 | (7H, m) |

PRODUCTION EXAMPLE 6

3-(2-chloro-6-fluorophenyl)-5-[4-(3-chloro-5-trifluoromethylpyridin-2-yloxy)phenyl]-1-methyl-1H-1,2,4-triazole (Compound No. 188)

A mixture of 1.30 g of N-methyl-N-phenylsulfonyl-2-chloro-6-fluorobenzohydrazonoyl chloride, 1.00 g of 4-(3-chloro-5-trifluoromethylpyridin-2-yloxy)benzonitrile, 0.50 g of anhydrous aluminum chloride and 3 ml of o-dichlorobenzene was stirred in an oil bath at a temperature of 140° C. for 30 minutes. After the cooling, the resulting solution was dissolved in 100 ml of chloroform, washed with diluted hydrochloric acid solution, diluted sodium hydroxide solution and saline water in this order, dried over anhydrous magnesium sulfate and concentrated under a reduced pressure. The resulting concentrate was purified through a chromatography of silica gel column using a mixed solution of hexane and ethyl acetate as a developing solvent to obtain 0.70 g of the given compound (measurement of n$_D^{20}$ was impossible). NMR data (60 MHz, CDCl$_3$ solvent, δ value)

| 4.07 | (3H, s) |
|---|---|
| 6.75–8.58 | (9H, m) |

PRODUCTION EXAMPLE 7

N-methyl-N-phenylsulfonyl-2-chlorobenzamidrazone

In 100 ml of N,N-dimethylformamide was dissolved 17.2 g of N-methyl-N-phenylsulfonyl-2-chlorobenzhydrazonoyl chloride, which was stirred at 60°–70° C. for 3 hours while introducing ammonia gas thereinto. After the cooling, the reaction solution was dissolved in 500 ml of ethyl acetate, washed with water, dried on anhydrous magnesium sulfate and concentrated under a reduced pressure. The resulting crystal was washed with n-hexane to obtain 15.4 g of the given compound (melting point 94.0°–96.0° C.).

| NMR data (60 MHz, CDCl$_3$ solvent, δ value) | |
|---|---|
| 2.75 | (3H, s) |
| 5.80 | (2H, s) |
| 7.10–8.00 | (9H, m) |

The insecticide and acaricide according to the invention contain the triazole derivative represented by the general formula (I) as an active ingredient.

When the triazole compounds according to the invention are used as an active ingredient for insecticides and acaricides, these compounds themselves may be used alone, or may be compounded with a carrier, a surfactant, a dispersing agent, an adjuvant or the like usually used in the formulation to form dusts, wettable powder, emulsion, fine powder, granulates or the like.

As the carrier used in the formulation, mention may be made of a solid carrier such as zeeklite, talc, bentonite, clay, kaolin, diatomaceous earth, white carbon, vermiculite, calcium hydroxide, quartz sand, ammonium sulfate, urea or the like; and a liquid carrier such as isopropyl alcohol, xylene, cyclohexane, methylnaphthalene or the like.

As the surfactant and dispersing agent, mention may be made of a metal salt of alkylbenzene sulfonic acid, a metal salt of dinaphtylmethane disulfonic acid, a sulfuric acid ester of alcohol, alkylarylsulfonate, lignin sulfonate, polyoxyethylene glycol ether, polyoxyethylene alkylaryl ether, polyoxyethylene sorbitan monoalkylate and the like.

As the adjuvant, mention may be made of carboxymethylcellulose, polyethylene glycol, gum arabi and the like.

In use, the compound according to the invention is directly applied or sprayed by diluting to a proper concentration.

The insecticide and acaricide according to the invention may be used by spraying onto stem and leaves, by applying to soil, by applying to a nursery box, by spraying onto water surface or the like.

In the formulation, the amount of the active ingredient used may be selected in accordance with the use purpose, but it is properly selected within a range of 0.05-20% by weight, preferably 0.1-10% by weight in case of the dusts or granules. In case of the emulsion or wettable powder, the amount of the active ingredient is properly selected within a range of 0.5-80% by weight, preferably 1-60% by weight.

The amount of the insecticide and acaricide applied is dependent upon the kind of the compound used as an active ingredient, injurious insect to be controlled, tendency and degree of insect injury, environmental condition, kind of formulation used and the like. When the insecticide and acaricide according to the invention are directly used as dusts or granules, the amount of the active ingredient is properly selected within a range of 0.05 g-5 kg, preferably 0.1-1 kg per 10 are. Furthermore, when they are used in form of a liquid as emulsion or wettable powder, the amount of the active ingredient is properly selected within a range of 0.1-5000 ppm, preferably 1-1000 ppm.

Moreover, the insecticide and acaricide according to the invention may be used by mixing with other insecticide, fungicide, fertilizer, plant growth regulator and the like.

The formulation will concretely be described with respect to typical examples. In this case, the kind of the compounds and additives and the compounding ratio are not limited to these examples and may be varied within wide ranges. Moreover, % is by weight otherwise specified.

FORMULATION EXAMPLE 1

Emulsion

An emulsion was prepared by uniformly dissolving 30% of compound No. 55, 20% of cyclohexanone, 11% of polyoxyethylene alkylaryl ether, 4% of calcium alkylbenzenesulfonate and 35% of methylnaphthalene.

FORMULATION EXAMPLE 2

Wettable powder

A wettable powder was prepared by uniformly mixing and pulverizing 40% of compound No. 38, 15% of diatomaceous earth, 15% of clay, 25% of white carbon, 2% of sodium dinaphthylmethane disulfonate and 3% of sodium lignin sulfonate. FORMULATION EXAMPLE 3

Dust

A dust was prepared by uniformly mixing and pulverizing 2% of compound No. 120, 5% of diatomaceous earth and 93% of clay.

FORMULATION EXAMPLE 4

Granules

A mixture of 5% of compound No. 71, 2% of sodium salt of lauryl alcohol sulfuric acid ester, 5% of sodium lignin sulfonate, 2% of carboxymethyl cellulose and 86% of clay was uniformly pulverized and added with 20 parts by kneaded, shaped into granules of 14-32 mesh through an extrusion type granulating machine and dried to form granules.

The triazole derivatives according to the invention are effective to control planthoppers such as brown planthopper, white-backed planthopper, small brown planthopper and the like; leafhoppers such as green rice leafhopper, tea green leafhopper and the like; aphids such as cotton aphid, green peach aphid, cabbage aphid and the like; whiteflies such as greenhouse whitefly and the like; hemipteran injurious insects such as mulberry scale, corbett rice bug and the like; lepidopteran injurious insects such as diamond-back moth, lima-bean cutworm, tobacco cutworm and the like; dipteran injurious insects such as house maggot, mosquito and the like; elytron injurious insects such as rice plant weevil, soy bean weevil, cucurbit leaf beetle and the like; orthopteran injurious insects such as american cockroach, steam fly and the like; mites such as two-spotted spider mite, kanzawa spider mite, citrus red mite and the like; and mites having an increased resistance to organotin, synthesized pyrethroid and organophosphorus chemicals.

Particularly, they develop a very excellent effect of controlling mites such as two-spotted spider mite, kanzawa spider mite, citrus red mite and the like.

The effect of the compounds according to the invention will be described with respect to the following test examples. Moreover, the following compounds were used as a comparative chemical, wherein a comparative chemical a is a compound described in Japanese Patent laid open No. 56-154464, and a comparative chemical b is a commercial product usually used for the control of mites.

COMPARATIVE CHEMICAL A 3,5-bis(o-chlorophenyl)-1-methyl-1H-1,2,4-triazole

COMPARATIVE CHEMICAL B

Hexythiazox (common name)

Test Example 1

Insecticidal test for diamond-back moth

The wettable powder prepared according to Formulation Example 2 was diluted with water so that the concentration of the active ingredient was 500 ppm.

Cabbage leaves were immersed in the resulting diluted solution, dried in air and then placed in a vinyl chloride cup of 60 ml capacity. Ten larvae of 3rd instar diamond-back moth were released in the cup and thereafter a cover was placed thereon. Then, the cup was placed in a thermostatic chamber of 25° C. for 6 days, and the number of larvae died was counted to calculate the percentage of mortality. The test was carried out by double series. Moreover, the comparative chemical A was used for the comparison. The results are shown in Table 11.

TABLE 11

| Compound No. | Mortality (%) |
| --- | --- |
| 17 | 100 |
| 18 | 90 |
| 30 | 100 |
| 31 | 95 |
| 35 | 95 |
| 37 | 100 |
| 39 | 90 |
| 43 | 100 |
| 47 | 90 |
| 68 | 90 |
| 71 | 100 |
| 114 | 95 |
| 120 | 100 |
| 137 | 90 |
| Comparative chemical A | 20 |

TEST EXAMPLE 2

Insecticidal test for larvae of cotton aphid

The wettable powder prepared according to Formulation Example 2 was diluted with water so that the concentration of the active ingredient was 100 ppm. In the resulting diluted solution were immersed cucumber seedlings previously inoculated with larvae of cotton aphid and then subjected to a drying treatment in air. After the treatment, the cucumber seedlings were placed in a thermostatic chamber of 25° C. for 3 days and then the number of larvae died was counted to calculate the percentage of mortality. The test was carried out by double series. The results are shown in Table 12.

TABLE 12

| Compound No. | Mortality (%) | Compound No. | Mortality (%) |
| --- | --- | --- | --- |
| 3 | 100 | 103 | 100 |
| 13 | 100 | 104 | 100 |
| 14 | 100 | 105 | 100 |
| 15 | 100 | 106 | 100 |
| 17 | 100 | 107 | 100 |
| 19 | 100 | 108 | 100 |
| 30 | 100 | 109 | 100 |
| 35 | 100 | 111 | 100 |
| 39 | 100 | 112 | 100 |
| 47 | 100 | 113 | 100 |
| 51 | 100 | 114 | 100 |
| 55 | 100 | 117 | 100 |
| 68 | 100 | 118 | 100 |
| 69 | 100 | 119 | 100 |
| 71 | 100 | 120 | 100 |
| 84 | 100 | 127 | 100 |
| 87 | 100 | 131 | 100 |
| 93 | 100 | 137 | 100 |
| 96 | 100 | 179 | 100 |
| 97 | 100 | 180 | 100 |
| 100 | 100 | 229 | 100 |
| 101 | 100 | | |

TEST EXAMPLE 3

Ovicidal test for eggs of two-spotted spider mite

Female adults of two-spotted spider mite were placed on three leaf discs of kidney bean (diameter: 15 mm) and oviposited over 24 hours, and thereafter these adults were removed therefrom. The wettable powder prepared according to Formulation Example 2 was diluted with water so that the concentration of the active ingredient was 0.16 ppm. In the resulting diluted solution were immersed these leaf discs for 10 seconds. After the treatment, the leaf discs were placed in a thermostatic chamber of 25° C. for 7 days and then the number of unhatched eggs was counted to calculate the percentage of ovicidal activity. The test was carried out by double series. Moreover, the comparative chemicals A and B were used for the comparison. The results are shown in Table 13.

TABLE 13

| Compound No. | Ovicidal activity (%) |
| --- | --- |
| 21 | 100 |
| 30 | 100 |
| 34 | 100 |
| 35 | 100 |
| 38 | 100 |
| 39 | 95 |
| 42 | 100 |
| 43 | 95 |
| 47 | 100 |
| 50 | 100 |
| 51 | 100 |
| 54 | 100 |
| 55 | 100 |
| Comparative chemical A | 24 |
| Comparative chemical B | 95 |

TEST EXAMPLE 4

Ovicidal test for eggs of chemical-resistant kanzawa spider mite

Female adults of kanzawa spider mite having a resistance to commercially available chemicals were placed on three lead disc of kidney bean (diameter: 15 mm) and oviposited over 2 days, and thereafter these adults were removed therefrom. The wettable powder prepared according to Formulation Example 2 was diluted with water so that the concentration of the active ingredient was 4 ppm. In the resulting diluted solution were immersed these leaf discs for 10 seconds. After the treatment, the leaf discs were placed in a thermostatic chamber of 25° C. for 7 days and then the number of unhatched eggs was counted to calculate the percentage of ovicidal activity. The test was carried out by double series. Moreover, the comparative chemicals A and B were used for the comparison. The results are shown in Table 14.

TABLE 14

| Compound No. | Ovicidal activity (%) | Compound No. | Ovicidal activity (%) |
| --- | --- | --- | --- |
| 3 | 100 | 53 | 90 |
| 13 | 100 | 55 | 100 |
| 14 | 100 | 56 | 100 |
| 15 | 100 | 57 | 90 |
| 21 | 100 | 84 | 90 |
| 30 | 100 | 106 | 100 |
| 34 | 100 | 108 | 90 |
| 35 | 100 | 110 | 100 |

TABLE 14-continued

| Compound No. | Ovicidal activity (%) | Compound No. | Ovicidal activity (%) |
| --- | --- | --- | --- |
| 36 | 100 | 111 | 95 |
| 37 | 100 | 112 | 100 |
| 38 | 100 | 117 | 100 |
| 39 | 100 | 118 | 100 |
| 40 | 100 | 155 | 100 |
| 41 | 100 | 156 | 100 |
| 42 | 100 | 157 | 100 |
| 43 | 100 | 180 | 100 |
| 44 | 100 | 181 | 100 |
| 46 | 90 | 182 | 100 |
| 48 | 100 | Comparative chemical A | 31 |
| 51 | 100 | | |
| 52 | 95 | Comparative chemical B | 0 |

TEST EXAMPLE 5

Insecticidal test for larvae of chemical-resistant kanzawa spider mite

Female adults of kanzawa spider mite having a resistance to commercially available chemicals were placed on three leaf discs of kidney bean (diameter: 15 mm) and oviposited over 2 days, and thereafter these adults were removed therefrom. Then, these leaf discs were placed in a thermostatic chamber of 25° C. for 5 days and the number of hatched larvae was counted. Separately, the wettable powder prepared according to Formulation Example 2 was diluted with water so that the concentration of the active ingredient was 20 ppm. After these leaf discs were sprayed with the resulting diluted solution, they were placed in a thermostatic chamber of 25° C. for 7 days and then the number of living adults was counted to calculate the percentage of mortality on the hatched larvae. The test was carried out by double series. Moreover, the comparative chemicals A and B were used for the comparison. The results are shown in Table 15.

TABLE 15

| Compound No. | Mortality (%) | Compound No. | Mortality (%) |
| --- | --- | --- | --- |
| 3 | 100 | 41 | 100 |
| 13 | 100 | 42 | 100 |
| 14 | 100 | 43 | 100 |
| 15 | 100 | 44 | 100 |
| 16 | 100 | 45 | 100 |
| 17 | 100 | 46 | 100 |
| 18 | 100 | 47 | 100 |
| 21 | 100 | 48 | 100 |
| 30 | 100 | 49 | 100 |
| 31 | 100 | 50 | 100 |
| 32 | 100 | 51 | 100 |
| 34 | 100 | 52 | 100 |
| 35 | 100 | 53 | 100 |
| 36 | 100 | 55 | 100 |
| 37 | 100 | 56 | 100 |
| 38 | 100 | Comparative chemical A | 55 |
| 39 | 100 | | |
| 40 | 100 | Comparative chemical B | 25 |

TEST EXAMPLE 6

Ovicidal test for eggs of citrus red mite

Female adults of citrus red mite were placed on two laminae of citrus fruit (diameter: 10 mm) and oviposited over 2 days, and thereafter these adults were removed therefrom. The wettable powder prepared according to Formulation Example 2 was diluted with water so that the concentration of the active ingredient was 4 ppm. In the resulting diluted solution were immersed these laminae for 10 seconds. After the treatment, the laminae were placed in a thermostatic chamber of 25° C. for 7 days and then the number of unhatched eggs was counted to calculate the percentage of ovidcidal activity. The test was carried out by double series. Moreover, the comparative chemicals A and B were used for the comparison. The results are shown in Table 16.

TABLE 16

| Compound No. | Ovicidal activity (%) |
| --- | --- |
| 3 | 95 |
| 16 | 90 |
| 17 | 100 |
| 18 | 100 |
| 21 | 95 |
| 30 | 100 |
| 31 | 100 |
| 32 | 100 |
| 34 | 100 |
| 35 | 100 |
| 36 | 95 |
| 37 | 100 |
| 38 | 100 |
| 39 | 100 |
| 40 | 90 |
| 43 | 100 |
| 44 | 100 |
| 47 | 95 |
| 48 | 100 |
| 52 | 100 |
| 97 | 95 |
| 106 | 100 |
| Comparative chemical A | 33 |
| Comparative chemical B | 90 |

What is claimed is:

1. A triazole derivative having the following formula:

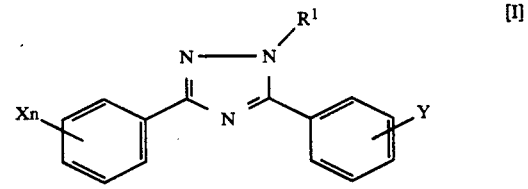

[I]

wherein $R^1$ is alkyl ($C_1$-$C_6$) group, x is a hydrogen atom, a halogen atom, an alkyl ($C_1$-$C_6$) group, an alkoxy ($C_1$-$C_6$) group, an alkylthio ($C_1$-$C_6$) group, a nitro group, a cyano group or a trifluoromethyl group, n is an integer of 1-5 provided that when n is 2 or more, X may be an optional combination of same or different atoms or groups and Y is an alkyl ($C_7$-$C_{20}$) group, an alkoxy ($C_7$-$C_{20}$) group, an alkylthio ($C_7$-$C_{20}$) group, an alkylsulfinyl ($C_7$-$C_{20}$) group, an alkylsulfonyl ($C_7$-$C_{20}$) group, an alkenyl ($C_2$-$C_{20}$) group, an alkynyl ($C_2$-$C_{20}$) group, an alkoxy ($C_1$-$C_{12}$) alkyl ($C_1$-$C_6$) group, an alkoxy ($C_1$-$C_6$) alkoxy ($C_1$-$C_6$) group, an alkylthio ($C_1$-$C_6$) alkyl ($C_1$-$C_6$) group, a cycloalkyl ($C_3$-$C_{12}$) group, a cycloalkyl ($C_3$-$C_{12}$) alkyl ($C_1$-$C_6$) group, a cycloalkyl ($C_3$-$C_{12}$) alkoxy ($C_1$-$C_6$) group, a cycloalkyl ($C_3$-$C_{12}$) alkenyl ($C_2$-$C_6$) group, a cycloalkyl ($C_3$-$C_{12}$) alkynyl ($C_2$-$C_6$) group, a trialkyl ($C_1$-$C_4$) silyalkyl ($C_1$-$C_4$) group, a trialkyl ($C_1$-$C_4$) silyalkoxy ($C_1$-$C_4$) group or a group represented by the following formula (1):

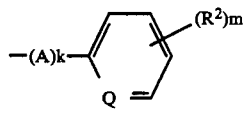

(wherein A is an oxygen atom, a sulfur atom, an alkylene ($C_1$-$C_4$) group, an alkyleneoxy ($C_1$-$C_4$) group, an oxyalkylene ($C_1$-$C_4$) group or an alkyleneoxy ($C_1$-$C_4$) alkylene ($C_1$-$C_4$) group, k is 0 or 1, Q is —CH= group, $R^2$ is a hydrogen atom, a halogen atom, an alkyl ($C_1$-$C_6$) group, an alkoxy ($C_1$-$C_6$) group, a trifluoromethyl group or a trifluoromethoxy group and m is an integer of 1-5 provided that when m is 2 or more, $R^2$ may be an optional combination of same or different atoms or groups.)

2. The triazole derivative according to claim 1, wherein said $R^1$ is a straight or branched-chain alkyl ($C_1$-$C_6$) group, X is a hydrogen atom, a halogen atom, a straight or branched-chain alkyl ($C_1$-$C_4$) group, a nitro group, a cyano group or a trifluoromethyl group, n is an integer of 1-3 provided that when n is 2 or 3, X may be an optional combination of same or different atoms or groups, Y is a straight or branched-chain alkyl ($C_7$-$C_{16}$) group, a cycloalkyl ($C_3$-$C_{12}$) group, a cycloalkyl ($C_3$-$C_6$) alkyl ($C_1$-$C_6$) group, a straight or branched-chain alkoxy ($C_{10}$-$C_{12}$) group, a cycloalkyl ($C_3$-$C_6$) alkoxy ($C_1$-$C_6$) group, a straight or branched-chain alkylthio ($C_8$)-$C_{12}$) group, an alkylsulfinyl ($C_8$-$C_{12}$) group, an alkylsulfonyl ($C_8$-$C_{12}$) group, a straight or branched-chain alkenyl ($C_8$-$C_{12}$) group, a cycloalkyl ($C_3$-$C_6$) alkenyl ($C_2$-$C_6$) group, a straight or branched-chain alkynyl ($C_3$-$C_{12}$) group, a cycloalkyl ($C_3$-$C_6$) alkynyl ($C_2$-$C_6$) group, a tris silyalkyl ($C_1$-$C_4$) group, a tris silylalkoxy ($C_1$-$C_4$) group or a group represented by said formula (1) (wherein A is an oxygen atom, a sulfur atom, an alkylene ($C_1$-$C_2$) group, an alkyleneoxy ($C_1$-$C_2$) group or an oxyalkylene ($C_1$-$C_2$) group, k is 0 or 1, Q is —CH= group, $R^2$ is a hydrogen atom, a halogen atom, an alkyl ($C_1$-$C_6$) group, an alkoxy ($C_1$-$C_4$) group, a trifluoromethyl group or a trifluoromethoxy group and m is an integer of 1-3 provided that when m is 2 or 3, $R^2$ may be an optional combination of same or different atoms or groups.)

3. The triazole derivative according to claim 1, wherein said $R^1$ is methyl gruop, X is halogen atom, n is 1 or 2 provided that when n is 2, X may be an optional combination of same or different atoms and Y is an alkyl ($C_{10}$-$C_{16}$) group.

4. The triazole derivative according to claim 1, wherein aid $R^1$ is methyl group, X is a chlorine atom or a fluorine atom, n is 1 or 2 provided that when n is 2, X may be an optional combination of same or different atoms and Y is a dodecyl group or a tris(methyl)silylmethoxy group.

5. The triazole derivative according to claim 1, wherein said Y is an alkoxy ($C_1$-$C_{12}$) alkyl ($C_1$-$C_6$) group, an alkoxy ($C_1$-$C_6$) alkoxy ($C_1$-$C_6$) group or an alkylthio ($C_1$-$C_6$) alkyl ($C_1$-$C_6$) group.

6. The triazole derivative according to claim 1, wherein said Y is a group represented by said formula (1) (wherein A is an oxygen atom, a sulfur atom, an alkylene ($C_1$-$C_4$) group, an alkyleneoxy ($C_1$-$C_4$) group, an oxyalkylene ($C_1$-$C_4$) group or an alkyleneoxy ($C_1$-$C_4$) alkylene ($C_1$-$C_4$) group, k is 0 or 1, Q is —CH= group, $R^2$ is a hydrogen atom, a halogen atom, an alkyl ($C_1$-$C_6$) group, an alkoxy ($C_1$-$C_6$) group, a trifluoromethyl group or a trifluoromethoxy group and m is an integer of 1-3 provided that when m is 2 or more, $R^2$ may be an optional combination of same or different atoms or groups.

7. The triazole derivative according to claim 1, wherein said $R^1$ is methyl group, X is a chlorine atom or a fluorine atom, n is 1 or 2 provided that when n is 2, X may be an optional combination of same or different atoms and Y is a group represented by said formula (1) (wherein A is an oxygen atom, a methylene group, a methyleneoxy group or an oxymethylene group, k is 0 or 1, Q is —CH= group, $R^2$ is a hydrogen atom, a chlorine atom, a fluorine atom, an alkyl ($C_1$-$C_4$) group, an alkoxy ($C_1$-$C_4$) group, a trifluoromethyl group or a trifluoromethoxy group, m is 1 or 2 provided that when m is 2, $R^2$ may be an optional combination of same or different atoms or groups.

8. An insecticidal and acaricidal composition comprising an insecticidally and acaricidally effective amount of triazole derivative as defined in claim 1 and a carrier.

9. An insecticidal and acaricidal composition comprising an insecticidally and acaricidally effective amount of triazole derivative as defined in claim 2 and a carrier.

10. An insecticidal and acaricidal composition comprising an insecticidally and acaricidally effective amount of triazole derivative as defined in claim 3 and a carrier.

11. An insecticidal and acaricidal composition comprising an insecticidally and acaricidally effective amount of triazole derivative as defined in claim 4 and a carrier.

12. An insecticidal and acaricidal composition comprising an insecticidally and acaricidally effective amount of triazole derivative as defined in claim 5 and a carrier.

13. An insecticidal and acaricidal composition comprising an insecticidally and acaricidally effective amount of triazole derivative as defined in claim 6 and a carrier.

14. An insecticidal and acaricidal composition comprising an insecticidally and acaricidally effective amount of triazole derivative as defined in claim 7 and a carrier.

15. A method of killing insects, aphids or mites or their eggs or larvae, comprising applying to a site infested or liable to infestation therewith an insecticidally and acaricidally effective amount of triazole derivative as defined in claim 1.

16. A method of killing insects, aphids or mites or their eggs or larvae, comprising applying to a site infested or liable to infestation therewith an insecticidally and acaricidally effective amount of triazole derivative as defined in claim 2.

17. A method of killing insects, aphids or mites or their eggs or larvae, comprising applying to a site infested or liable to infestation therewith an insecticidally and acaricidally effective amount of triazole derivative as defined in claim 3.

18. A method of killing insects, aphids or mites or their eggs or larvae, comprising applying to a site infested or liable to infestation therewith an insecticidally and acaricidally effective amount of triazole derivative as defined in claim 4.

19. A method of killing insects, aphids or mites or their eggs or larvae, comprising applying to a site infested or liable to infestation therewith an insecticidally and acaricidally effective amount of triazole derivative as defined in claim 5.

20. A method of killing insects, aphids or mites or their eggs or larvae, comprising applying to a site infested or liable to infestation therewith an insecticidally and acaricidally effective amount of triazole derivative as defined in claim 6.

21. A method of killing insects, aphids or mites or their eggs or larvae, comprising applying to a site infested or liable to infestation therewith an insecticidally and acaricidally effective amount of triazole derivative as defined in claim 7.

* * * * *